US012649016B2

(12) United States Patent
Lai et al.

(10) Patent No.: US 12,649,016 B2
(45) Date of Patent: Jun. 9, 2026

(54) BIOMEDICAL TAPE, PREPARATION METHOD THEREFOR, AND APPLICATION THEREOF

(71) Applicant: SHENZHEN INSTITUTES OF ADVANCED TECHNOLOGY, Shenzhen (CN)

(72) Inventors: Yuxiao Lai, Shenzhen (CN); Yuanchi Zhang, Shenzhen (CN); Wei Zhang, Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 360 days.

(21) Appl. No.: 18/044,681

(22) PCT Filed: Aug. 11, 2021

(86) PCT No.: PCT/CN2021/112116
§ 371 (c)(1),
(2) Date: Mar. 9, 2023

(87) PCT Pub. No.: WO2023/015497
PCT Pub. Date: Feb. 16, 2023

(65) Prior Publication Data
US 2023/0390451 A1 Dec. 7, 2023

(30) Foreign Application Priority Data
Aug. 9, 2021 (CN) .......................... 202110911399.9

(51) Int. Cl.
A61L 24/08 (2006.01)
A61L 24/00 (2006.01)
A61L 24/02 (2006.01)
A61L 24/06 (2006.01)
A61L 24/10 (2006.01)

(52) U.S. Cl.
CPC ........... *A61L 24/08* (2013.01); *A61L 24/0031* (2013.01); *A61L 24/02* (2013.01); *A61L 24/06* (2013.01); *A61L 24/104* (2013.01)

(58) Field of Classification Search
CPC ...... A61L 24/08; A61L 24/0031; A61L 24/02; A61L 24/06; A61L 24/104
See application file for complete search history.

(56) References Cited

U.S. PATENT DOCUMENTS

| | | | |
|---|---|---|---|
| 2009/0017091 A1 | 1/2009 | Daniloff et al. | |
| 2012/0053130 A1 | 3/2012 | Mathias et al. | |
| 2021/0106718 A1 | 4/2021 | Hong et al. | |

FOREIGN PATENT DOCUMENTS

| | | | |
|---|---|---|---|
| CN | 105906821 A | 8/2016 | |
| CN | 106975097 A | 7/2017 | |
| CN | 108912353 A | 11/2018 | |
| CN | 111973804 A | 11/2020 | |
| CN | 112791227 | * | 5/2021 |
| CN | 112791227 A | 5/2021 | |
| CN | 112933288 A | 6/2021 | |
| CN | 115702947 A | 2/2023 | |
| KR | 20130011354 A | 1/2013 | |
| WO | 2020167868 A1 | 8/2020 | |
| WO | 2023015497 A1 | 2/2023 | |

OTHER PUBLICATIONS

International Search Report for PCT/CN2021/112116 dated Apr. 26, 2022.
Written Opinion of the International Searching Authority for PCT/CN2021/112116 dated Apr. 26, 2022.
Hu, Z., Fu, S., and Tang, A. Fabrication of light-triggered AuNP/CNC/SMP nanocomposites, BioResources. 2017; 12(1), pp. 1982-1990.
Xiaojing Su, Hongqiang Li, Xuejun Lai, Zhonghua Chen, Xingrong Zeng. 3D porous superhydrophobic CNT/EVA composites for recoverable shape reconfiguration and underwater vibration detection. Advanced Functional Materials, 2019; 29:1900554.
Yang B W, Yin J H, Chen Y, et al. 2D-black-phosphorus-reinforced 3D-printed scaffolds: A stepwise countermeasure for osteosarcoma. Advanced Materials, 2018; 30(10):1705611.
Wentao Kan, et al. The Study on Release Mechanism of Hydrogel Piece as Drug Carrier. Materials Reports. 2013, 27(S1): 221-223.
Gao Yang, et al. A universal strategy for tough adhesion of wet soft material. Advanced Functional Materials. 2020, 30(36): 2003207.
China National Intellectual Property Administration. First search for CN Application No. 202110911399 and English translation, mailed Aug. 25, 2023, pp. 1-3.

* cited by examiner

*Primary Examiner* — Shirley V Gembeh
(74) *Attorney, Agent, or Firm* — D'Ambrosio & Menon, PLLC; Usha Menon

(57) ABSTRACT

Provided are a biomedical tape, a preparation method thereof and use thereof. The biomedical tape comprises a hydrogel carrier in dry state and a functional nanomaterial encapsulated within the hydrogel carrier in dry state, and the hydrogel carrier in dry state comprises a thin film body of hyaluronic acid hydrogel and a dopamine-modified polyacrylic acid permeated into a surface of the thin film body of hyaluronic acid hydrogel. The preparation method for the biomedical tape comprises: preparing a hyaluronic acid hydrogel with the functional nanomaterial dispersed therein, and drying and curing the hydrogel to form a film to obtain the thin film body of hyaluronic acid hydrogel; and preparing a dopamine-modified polyacrylic acid solution, and permeating the solution into a surface of the thin film body of hyaluronic acid hydrogel by coating to obtain the biomedical tape.

16 Claims, 3 Drawing Sheets

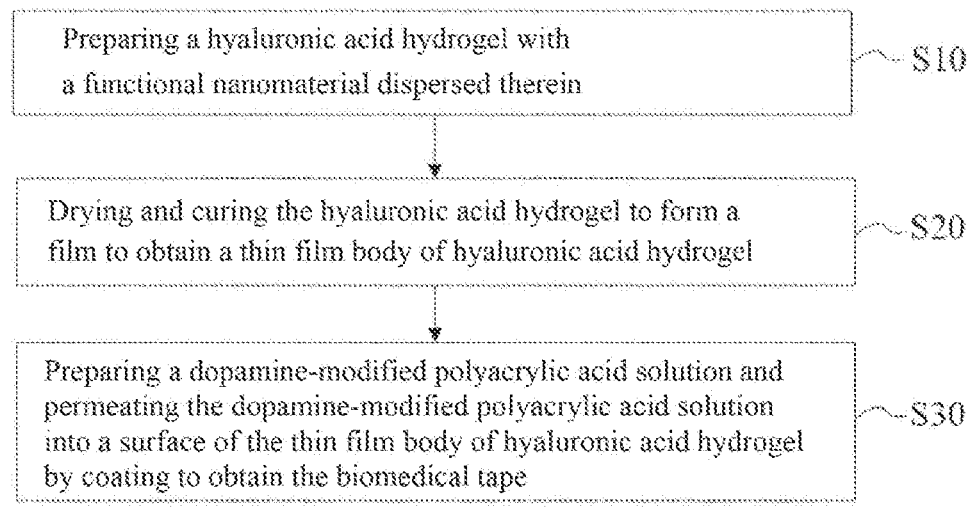

| | |
|---|---|
| Preparing a hyaluronic acid hydrogel with a functional nanomaterial dispersed therein | ~S10 |
| Drying and curing the hyaluronic acid hydrogel to form a film to obtain a thin film body of hyaluronic acid hydrogel | ~S20 |
| Preparing a dopamine-modified polyacrylic acid solution and permeating the dopamine-modified polyacrylic acid solution into a surface of the thin film body of hyaluronic acid hydrogel by coating to obtain the biomedical tape | ~S30 |

FIG. 1

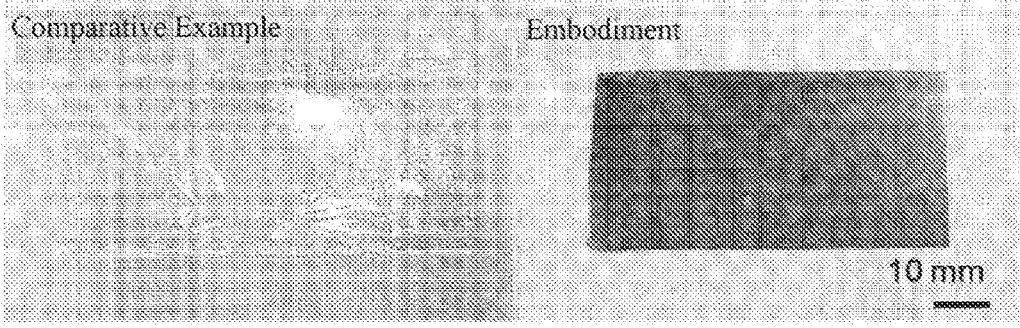

FIG. 2

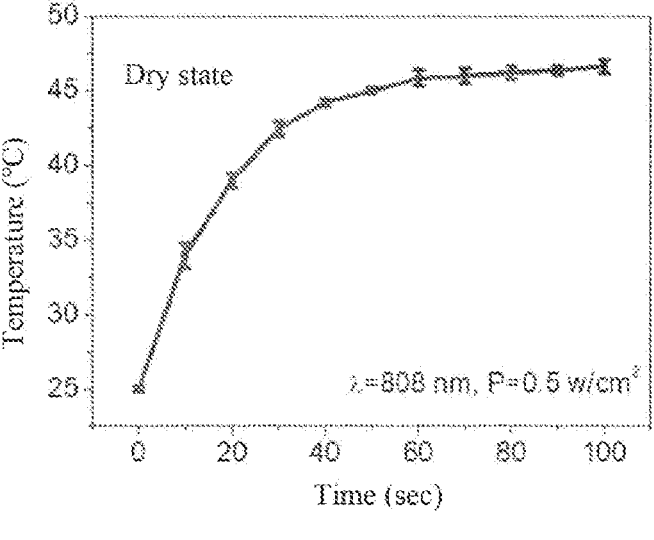

FIG. 3

BIOMEDICAL TAPE, PREPARATION METHOD THEREFOR, AND APPLICATION THEREOF

CROSS-REFERENCE TO RELATED APPLICATIONS

The present application is a national phase entry under 35 USC § 371 of International Application PCT/CN2021/112116, filed Aug. 11, 2021, which claims the benefit of and priority to Chinese Patent Application No. 2021109113999, filed Aug. 9, 2021, the entire disclosures of which are incorporated herein by reference.

TECHNICAL FIELD

The disclosure relates to the field of biomedical engineering technologies, and particularly to a biomedical tape, a preparation method thereof and use thereof.

BACKGROUND

Surgery is a common method for clinical treatment and control of most early solid tumors. However, there exist several thorny problems in the prognosis after surgical excision faces, and the most challenging one is tumor recurrence. For example, a postoperative recurrence rate of breast cancer ranges from 10% to 41%, most patients with recurrence also develop pulmonary metastasis or encephalic metastasis, and a mortality rate of patients suffering from postoperative recurrence is up to 90%. Therefore, in order to improve a survival, researches on prevention of tumor recurrence have been made continuously. In recent years, radiotherapy and chemotherapy have been postoperative treatment standards for tumor recurrence inhibition. However, a large number of literatures have reported the complications and side effects associated with radiotherapy and chemotherapy, such as immunosuppression, nephrotoxicity and cardiotoxicity. Therefore, a safe and effective postoperative treatment strategy for tumors has always been sought.

Photo-thermal therapy (PTT) is a treatment utilizing a photo-thermal effect of a nanofiller to kill residual cancer cells by near infrared (NIR) irradiation. Due to the simplicity, minimal invasion, low incidence of complications of the photo-thermal therapy, and the advantages such as high space and time accuracies of near infrared light, the photo-thermal therapy has attracted the interest of researchers. In order to obtain a better PTT performance, various nano-preparations have been explored as photo-thermal agents, such as gold nanoparticles (BioResources 2017, 12, 1982) and carbon nanotubes (Advanced Functional Materials 2019, 29, 1900554.). However, due to the limitations, such as poor biodegradability, of the photo-thermal agents, the clinical application of the PTT is still hindered. Black phosphorus (BP) is a new two-dimensional layered nano-material, with higher near infrared absorption capacity and higher photo-thermal conversion efficiency. More importantly, an application of a BP nanosheet in the field of tumors has been widely concerned due to the good biocompatibility and biodegradability.

However, at the presence of oxygen and/or water, the rapid degradation of the BP nanosheet hinders the practical application. Therefore, many researchers have introduced the BP nanosheet into various matrices to prepare composite materials. For example, Bowen Yang et al. integrated the BP nanosheet into a 3D printed bio-glass scaffold to improve the inherent instability (Advanced materials 2018, 30, 1705611). In recent years, different materials have been used as carriers to load functional nanofillers as dressings for postoperative treatment, such as silicon wafers, fibers, polymers and hydrogels. For dressings used in postoperative treatment of surgeries, such as a tumor surgery, in addition to biocompatibility and biodegradability, carrier matrices used should also have appropriate biomechanics and adhesion, so as to maintain treatment state and position, especially the latter. The main obstacle to the adhesion of the medical dressings in vivo is water at an interface between a material and a tissue, wherein a hydrogen bond can reduce an adhesion effect, while insufficient adhesion may lead to the deviation of a therapeutic effect and even cause adverse effects on a normal tissue.

SUMMARY

In order to solve the problem in the prior art that an dressing for postoperative treatment has a poor adhesion capability in biological aqueous environment, the disclosure provides a biomedical tape, a preparation method thereof and use thereof.

In order to achieve the above object, the disclosure adopts the following technical solution.

A biomedical tape comprises a hydrogel carrier in dry state and a functional nanomaterial encapsulated within the hydrogel carrier in dry state, wherein the hydrogel carrier in dry state comprises a thin film body of hyaluronic acid hydrogel and a dopamine-modified polyacrylic acid permeated into a surface of the thin film body of hyaluronic acid.

Specifically, the hyaluronic acid hydrogel is a double cross-linked hyaluronic acid hydrogel obtained by physical cross-linking and photochemical cross-linking reactions with methacrylic-anhydride-modified hyaluronic acid, polyvinyl alcohol and gelatin as raw materials.

Specifically, in the biomedical tape, an amount of the methacrylic-anhydride-modified hyaluronic acid is 12 wt % to 16 wt %, an amount of the polyvinyl alcohol is 65 wt % to 70 wt %, an amount of the gelatin is 5 wt % to 8 wt %, an amount of the functional nanomaterial is 0.1 wt % to 0.5 wt %, and an amount of the dopamine-modified polyacrylic acid is 10 wt % to 15 wt %.

Specifically, the functional nanomaterial is a black phosphorus nanosheet, a hydroxyapatite nanoparticle or a gold nanoparticle.

Specifically, a number-average molecular weight of the hyaluronic acid is 50,000 to 100,000, a number-average molecular weight of the polyvinyl alcohol is 6,000 to 20,000, and a number-average molecular weight of the polyacrylic acid is 3,000 to 6,000.

Specifically, based on a total mass of the methacrylic-anhydride-modified hyaluronic acid, the methacrylic-anhydride-modified hyaluronic acid comprises 98 wt % to 99.5 wt % of hyaluronic acid and 0.5 wt % to 2 wt % of methacrylic anhydride; and based on a total mass of the dopamine-modified polyacrylic acid, the dopamine-modified polyacrylic acid comprises 55 wt % to wt % of polyacrylic acid and 35 wt % to 45 wt % of dopamine.

In another aspect of the disclosure, provided is a preparation method for the above biomedical tape, which comprises:

preparing a hyaluronic acid hydrogel with a functional nanomaterial dispersed therein;

drying and curing the hyaluronic acid hydrogel to form a film to obtain a thin film body of hyaluronic acid hydrogel; and preparing a dopamine-modified polyacrylic acid solution, and permeating the dopamine-modified polyacrylic acid solution into a surface of the thin film body of hyaluronic acid hydrogel by coating to obtain the biomedical tape.

The preparing the hyaluronic acid hydrogel with the functional nanomaterial dispersed therein comprises:

preparing a methacrylic-anhydride-modified hyaluronic acid solution, a polyvinyl alcohol solution, a functional nanomaterial dispersion solution and a gelatin solution and mixing the solutions to obtain a mixed reaction solution; and performing physical cross-linking and photochemical cross-linking reactions on the mixed reaction solution at the presence of a cross-linking agent and a photoinitiator by illumination to obtain the hyaluronic acid hydrogel with the functional nanomaterial dispersed therein.

A mass concentration of the dopamine-modified polyacrylic acid solution is 5% to 10%.

The disclosure further provides use of the biomedical tape in the preparation of a biomedical dressing.

According to the biomedical tape provided by an embodiment of the disclosure, the hydrogel in dry state is used as the carrier of the functional nanomaterial, the dopamine-modified polyacrylic acid is permeated into the surface of the hydrogel carrier in dry state, so that the hydrogel carrier in dry state can be adhered to a tissue of a treatment site through chemical bonds and topological adhesion, and the biomedical tape is endowed with excellent adhesion capability in biological aqueous environment through the chemical bonds and topological adhesion, so as to maintain stable treatment state and position. The preparation method for the biomedical tape has relatively simple process, easy industrial implementation and wide applicability.

BRIEF DESCRIPTION OF THE DRAWINGS

FIG. 1 is a process flow chart of a preparation method for a biomedical tape in an embodiment of the disclosure;

FIG. 2 is an illustrative image of biomedical tapes prepared in an embodiment of the present disclosure and a comparative example;

FIG. 3 is a curve graph of a photo-thermal effect test of the biomedical tape in an embodiment of the disclosure in dry state;

DETAILED DESCRIPTION

Figure 4:
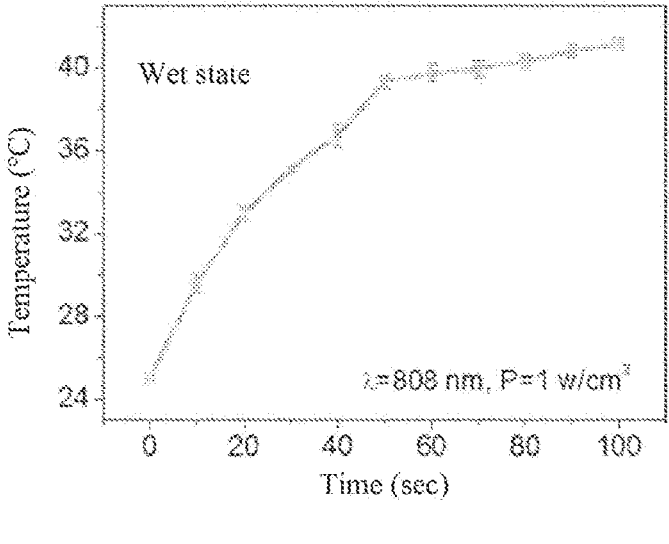
FIG. 4 is a curve graph of a photo-thermal effect test of the biomedical tape in an embodiment of the disclosure in wet state.

To make the objectives, features and advantages of the disclosure more obvious and understandable, the specific embodiments of the disclosure will be described in detail in combination with drawings, but these embodiments are merely exemplary and cannot be construed as limitation to the implementable range of the disclosure.

It should be noted that, in order to avoid obscuring the disclosure with unnecessary details, only the structures and/or processing steps closely related to the solution according to the disclosure are shown in the drawings, and other details having little relation with the disclosure are omitted.

As mentioned above, the dressings in the prior art used for postoperative treatment of surgery have poor adhesion capability in biological aqueous environment, which may lead to the deviation of a therapeutic effect and even cause adverse effects on a normal tissue. For the above problems in the prior art, an embodiment of the disclosure provides a biomedical tape, in which the carrier material is improved, so that the biomedical tape has excellent adhesion capability in biological aqueous environment.

An embodiment of the disclosure provides a biomedical tape first, which comprises a hydrogel carrier in dry state and a functional nanomaterial encapsulated within the hydrogel carrier in dry state, wherein the hydrogel carrier in dry state comprises a thin film body of hyaluronic acid hydrogel and a dopamine-modified polyacrylic acid (PAA-DA) permeated into a surface of the thin film body of hyaluronic acid hydrogel. The dopamine-modified polyacrylic acid is permeated into the surface of the hydrogel carrier in dry state, so that the hydrogel carrier in dry state can be adhered to a tissue of a treatment site through chemical bonds and topological adhesion, and the biomedical tape is endowed with excellent adhesion capability in biological aqueous environment through the chemical bonds and topological adhesion.

The thin film body of hyaluronic acid hydrogel is prepared by drying and curing a hyaluronic acid hydrogel to form a film. In a preferred solution, the hyaluronic acid hydrogel is a double cross-linked hyaluronic acid hydrogel obtained by physical cross-linking and photochemical cross-linking reactions with methacrylic-anhydride-modified hyaluronic acid (HAMA), polyvinyl alcohol (PVA) and gelatin (Gel) as raw materials.

In a preferred solution, in the biomedical tape, an amount of the methacrylic-anhydride-modified hyaluronic acid is 12 wt % to 16 wt %, an amount of the polyvinyl alcohol is 65 wt % to 70 wt %, an amount of the gelatin is 5 wt % to 8 wt %, an amount of the functional nanomaterial is 0.1 wt % to 0.5 wt %, and an amount of the dopamine-modified polyacrylic acid is 10 wt % to 15 wt %.

In a preferred solution, based on a total mass of the methacrylic-anhydride-modified hyaluronic acid, the methacrylic-anhydride-modified hyaluronic acid comprises 98 wt % to 99.5 wt % of hyaluronic acid (HA) and 0.5 wt % to 2 wt % of methacrylic anhydride (MA), and most preferably comprises 99.5 wt % of hyaluronic acid and 0.5 wt % of methacrylic anhydride; and based on a total mass of the dopamine-modified polyacrylic acid, the dopamine-modified polyacrylic acid comprises wt % to 65 wt % of polyacrylic acid (PAA) and 35 wt % to 45 wt % of dopamine (DA), and most preferably comprises 60 wt % of polyacrylic acid and 40 wt % of dopamine.

In a preferred solution, a number-average molecular weight of the hyaluronic acid is 50,000 to 100,000, and more preferably 60,000 to 80,000; a number-average molecular weight of the polyvinyl alcohol is 6,000 to 20,000, and more preferably 9,000 to 10,000; and a number-average molecular weight of the polyacrylic acid is 3,000 to 6,000, and more preferably 5,000.

The functional nanomaterial may be selected according to actual requirements, and is specifically selected and determined according to a surgery type of postoperative treatment of a surgery in which the biomedical tape is applied and a treatment item.

In a specific embodiment of the disclosure, the biomedical tape is used as a biomedical dressing for preventing tumor recurrence after tumor surgery, and residual cancer cells are killed by photo-thermal therapy after tumor excision, so that in the specific embodiment of the disclosure, the black phosphorus nanosheet is selected as the functional nanomaterial.

Further preferably, a thickness of the black phosphorus nanosheet is selected to be 10 nm to 100 nm, and a transverse dimension of the nanosheet is 100 nm to 1 μm.

In other embodiments, the functional nanomaterial may also be selected to be a hydroxyapatite nanoparticle for bone injury repair or a gold nanoparticle for conducting sensing.

The embodiment of the disclosure provides use of the biomedical tape above in the preparation of a biomedical dressing, and the biomedical tape is adhered to a tissue of a surgical site for corresponding postoperative treatment after surgery.

The embodiment of the disclosure provides a preparation method for the above biomedical tape, and with reference to FIG. 1, the preparation method comprises the following steps.

In S10, a hyaluronic acid hydrogel with a functional nanomaterial dispersed therein is prepared.

Firstly, a methacrylic-anhydride-modified hyaluronic acid solution, a polyvinyl alcohol solution, a functional nanomaterial dispersion solution and a gelatin solution are prepared, and the solutions are mixed to obtain a mixed reaction solution; and then physical cross-linking and photochemical cross-linking reactions are performed on the mixed reaction solution at the presence of a cross-linking agent and a photoinitiator by illumination to obtain the hyaluronic acid hydrogel with the functional nanomaterial dispersed therein.

In a specific technical solution, the step S10 comprises the following steps.

In S11, the methacrylic-anhydride-modified hyaluronic acid solution is prepared: hyaluronic acid is placed in a round-bottom flask and added with deionized water and dimethylformamide (DMF) as solvents to dissolve the hyaluronic acid to obtain the hyaluronic acid solution; the hyaluronic acid solution is adjusted to be weakly alkaline (pH=8.5 to 9) in an ice bath state, and then a methacrylic anhydride solution is added for reaction; the reaction solution is dialyzed with deionized water and then freeze-dried to obtain a methacrylic-anhydride-modified hyaluronic acid; and the prepared methacrylic-anhydride-modified hyaluronic acid is dissolved in deionized water to prepare the methacrylic-anhydride-modified hyaluronic acid solution.

In S12, a cross-linking agent is added into the methacrylic-anhydride-modified hyaluronic acid solution obtained in the step S11, for example, the cross-linking agent is 1-(3-dimethylaminopropyl)-3-ethylcarbodiimide hydrochloride (EDC) and N-hydroxysuccinimide (NHS).

In S13, the polyvinyl alcohol solution is prepared, and the polyvinyl alcohol solution and a photoinitiator are sequentially added into the solution obtained in the step S12, wherein a mass concentration of the polyvinyl alcohol solution is preferably 10% to 40%, and more preferably 20% to 30%. For example, 12959 is selected as the photoinitiator.

After adding the polyvinyl alcohol solution and the photoinitiator, the mixture is stirred and mixed, and then stood until no bubbles continue to emerge, and then a bubble layer on a liquid surface is sucked out.

In S14, the functional nanomaterial dispersion solution is prepared, and the functional nanomaterial dispersion solution is added into the solution obtained in the step S13.

In S15, the gelatin solution is prepared, and the gelatin solution is added into the solution obtained in the step S14 and stirred to obtain the mixed reaction solution.

A mass concentration of the gelatin solution is preferably 10% to 40%, and more preferably 20% to 30%.

In S16, the mixed reaction solution is irradiated with ultraviolet light to subject the mixed reaction solution to a cross-linking reaction to obtain the hyaluronic acid hydrogel with the functional nanomaterial dispersed therein.

In S20, the hyaluronic acid hydrogel is dried and cured to form a film to obtain a thin film body of hyaluronic acid hydrogel. Specifically, the hyaluronic acid hydrogel obtained in the step S16 above may be placed in a glass mold and naturally dried under a ventilated condition to obtain the thin film body of hyaluronic acid hydrogel, in which the functional nanomaterial is encapsulated.

In S30, a dopamine-modified polyacrylic acid solution is prepared, and the dopamine-modified polyacrylic acid solution is permeated into a surface of the thin film body of hyaluronic acid hydrogel by coating to obtain the biomedical tape.

In a specific technical solution, the step S30 comprises the following steps.

In S31, the dopamine-modified polyacrylic acid solution is prepared: polyacrylic acid and dopamine are placed in a three-neck flask and added with EDC and NHS as cross-linking agents, nitrogen is introduced at room temperature and stirred for reaction, and the mixture is sucked into a centrifugal tube for freeze-drying after the reaction is completed to obtain a dopamine-modified polyacrylic acid; and the prepared dopamine-modified polyacrylic acid is dissolved in deionized water to prepare the dopamine-modified polyacrylic acid solution.

In a preferred solution, a mass concentration of the dopamine-modified polyacrylic acid solution is 5% to 10%.

In S32, the dopamine-modified polyacrylic acid solution obtained in the step S31 is dripped and coated on a surface of the thin film body of hyaluronic acid hydrogel obtained in the step S20, and the dopamine-modified polyacrylic acid solution is permeated into the thin film body, thus preparing the biomedical tape.

Embodiment 1

The embodiment provides a biomedical tape for preventing tumor recurrence and a preparation method thereof.

The biomedical tape comprises a hydrogel carrier in dry state and a black phosphorus nanosheet encapsulated within the hydrogel carrier in dry state, wherein the hydrogel carrier in dry state comprises a thin film body of hyaluronic acid hydrogel and a dopamine-modified polyacrylic acid permeated into a surface of the thin film body of hyaluronic acid hydrogel.

The preparation method for the biomedical tape was as follows.

(1) Preparation of HAMA 2 g of HA was placed in a round-bottomed flask, and added with 100 mL of deionized water and 100 mL of DMF, then a flask stopper was plugged, and the mixture was stirred with a stirrer for two days, wherein HA with a number-average molecular weight of 80,000 was selected.

A pH of a solution system was adjusted to be weakly alkaline in an ice bath state, and then 10 mL of MA was added to react for two days, during which ice was replaced once every morning and evening.

The above mixed reaction solution was encapsulated with a dialysis bag in a 5 L beaker (which should not exceed ⅓ of a volume of the dialysis bag), and dialyzed with deionized water for three days, during which water was replaced once every morning and evening.

The solution was freeze-dried at −80° C. for 72 hours to obtain a HAMA product.

(2) Preparation of PAA-DA 4.32 g of PAA and 2.88 g of DA were added into a three-necked flask and added with 2.88 g of EDC and 1.73 g of NHS as cross-linking agents, nitrogen was introduced and stirred at room temperature for reaction for 24 hours, and then the mixture was sucked into a centrifuge tube.

The mixture was freeze-dried at −80° C. for 72 hours to obtain a PAA-DA product, and then the product was sealed and stored in a refrigerator at −80° C. until use.

In this embodiment, PAA with a number-average molecular weight of 5,000 was selected, and a mass fraction was 50%.

(3) Preparation of Biomedical Tape 60 mg of HAMA product prepared in the step (1) was dissolved in 1 mL of deionized water to prepare a HAMA solution.

60.5 mg of EDC and 36.4 mg of NHS were added into the HAMA solution and fully stirred to form a first solution.

1 mL of PVA solution with a concentration of 30 wt % and 18 mg of I2959 photoinitiator were added into the first solution, fully stirred and then stood until no bubbles continued to emerge, and a bubble layer on a liquid surface was sucked out to form a second solution. PVA with a number-average molecular weight of 10,000 was selected.

1 mL of BP solution with a concentration of 1 mg/mL was added into the second solution and stirred to form a third solution.

1 mL of Gel solution with a concentration of 30 wt % was added into the third solution, stirred quickly for about 30 seconds, then sucked into a glass mold, and cross-linked with 365 nm ultraviolet light for 5 minutes, and the cross-linked hydrogel was dried in a fume hood overnight to obtain the thin film body of hydrogel.

50 mg of the PAA-DA product prepared in the step (2) was dissolved in 1 mL of deionized water to prepare a PAA-DA solution with a concentration of 5 wt %, and the PAA-DA solution was dripped and coated on a surface of the dried hydrogel thin film body, and stood for 1 minute to 3 minutes, so that the PAA-DA solution was permeated into the hydrogel thin film body, thus preparing the biomedical tape.

Comparative Example

Compared with the embodiment, the comparative example was only different in that: the BP nanosheet or other functional nanomaterials were not added during the preparation of the biomedical tape.

Test Example

According to Embodiment 1 and Comparative Example, several biomedical tape samples of Embodiment 1 of the disclosure and several biomedical tape samples of Comparative Example were prepared respectively, and the following related performance tests were carried out. FIG. 2 shows an illustrative image of biomedical tapes prepared in Embodiment 1 and Comparative Example.

Test 1: Photo-Thermal Effect Test (1) The biomedical tape samples of Embodiment 1 of the disclosure were irradiated by near infrared light (with a wavelength of 808 nm and a power density of 0.5 w/cm2) in a dry state, and a temperature as function of time was recorded to obtain a curve graph of change of temperature as shown in FIG. 3.

(2) The biomedical tape samples of Embodiment 1 of the disclosure were irradiated by near infrared light (with a wavelength of 808 nm and a power density of 1 w/cm2) in a wet state, and a temperature as function of time was recorded to obtain a curve graph of change of temperature as shown in FIG. 4.

(3) The biomedical tape samples of Comparative Example were irradiated by near infrared light (with a wavelength of 808 nm and a power density of 0.5 w/cm2) in a dry state, and a temperature as function of time was recorded.

It could be seen from the above test that: the biomedical tape samples of Embodiment 1 of the disclosure had a good photo-thermal effect, and the biomedical tape samples could quickly reach 40° C. to 45° C. within 100 seconds in the dry or wet state, wherein heat dissipation in the wet state was faster, so that the temperature was lower than that in the dry state. The biomedical tape samples of Comparative Example were not added with a photo-thermal agent of a BP nanosheet, and no photo-thermal effect was observed.

Figure 5:
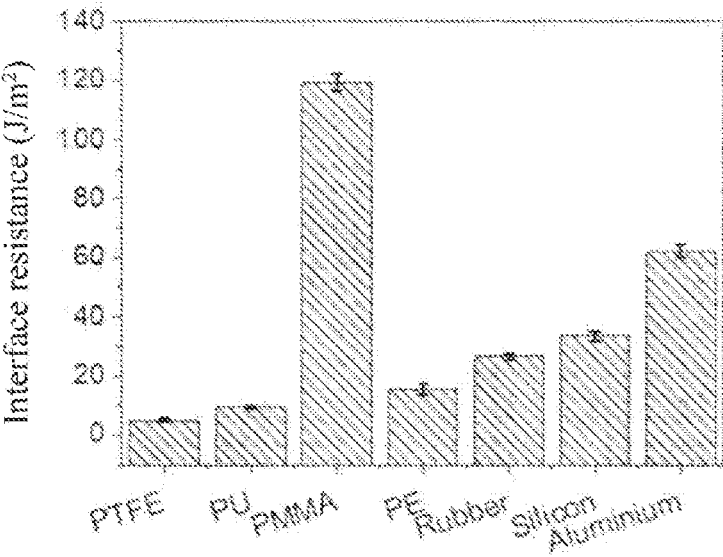
FIG. 5 is a data graph of an adhesion capability test of the biomedical tape in an embodiment of the disclosure to different materials.

Test 2: Adhesion Performance Test (1) The biomedical tape samples of Embodiment 1 of the disclosure were adhered to different materials to test adhesion performance parameters, wherein the different materials comprised PTFE (polytetrafluoroethylene), PU (polyurethane), PMMA (polymethylmethacrylate), PE (polyethylene), Rubber, Silicon and Aluminum. Test results referred to FIG. 5, and it could be seen from FIG. 5 that the biomedical tape samples provided by the embodiment of the disclosure all had a good adhesion capability to the different materials, especially had a greater adhesion capability to PMMA.

Figure 6:
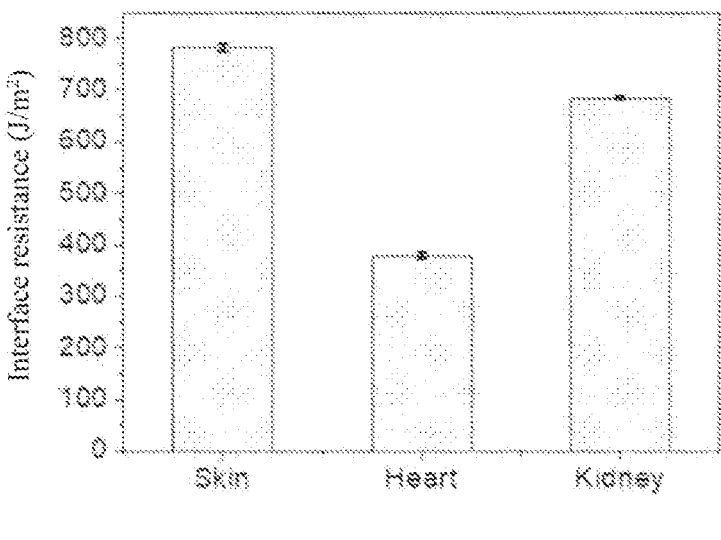
FIG. 6 is a data graph of an adhesion capability test of the biomedical tape in an embodiment of the disclosure to a biological tissue.

(2) The biomedical tape samples of Embodiment 1 of the disclosure were adhered to different biological tissues to test adhesion performance parameters, wherein the different biological tissues comprised Skin, Heart and Kidney from a pig. Test results referred to FIG. 6, and it could be seen from FIG. 6 that the biomedical tape samples provided by the embodiment of the disclosure all had a great adhesion capability to the biological tissues, indicating that the biomedical tape samples provided by the disclosure had excellent adhesion capability in biological aqueous environment.

Test 3: Mechanical Performance Test

Figure 7:
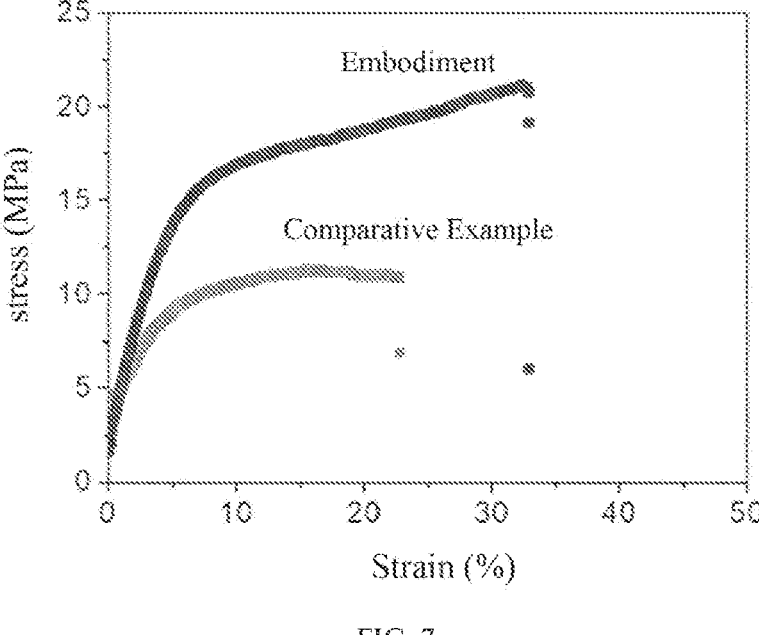
FIG. 7 is a stress-strain curve graph of the biomedical tapes in an embodiment of the disclosure and a comparative example.

Tensile tests were carried out on the biomedical tape samples of Embodiment 1 and the biomedical tape samples of Comparative Example, and the corresponding stress-strain curves were shown in FIG. 7. It could be seen from FIG. 7 that the biomedical tape samples provided by the embodiment of the disclosure had a good mechanical performance, and compared with Comparative Example without the functional nanomaterial, a tensile strength, a modulus and a ductility of the biomedical tape were greatly improved upon the functional nanomaterial was added into the biomedical tape samples of the embodiment of the disclosure.

In conclusion, for the biomedical tape provided by the embodiment of the disclosure, the dopamine-modified poly-acrylic acid is permeated into the surface of the dry state hydrogel carrier, so that the hydrogel carrier in dry state can be adhered to a tissue of a treatment site through chemical bonds and topological adhesion, and the biomedical tape is endowed with excellent adhesion capability in biological aqueous environment through chemical bonds and topological adhesion.

The above embodiments with specific and detailed description merely represent several embodiments according to the present disclosure, and it should be understood that for those of ordinary skill in the art, variations and modifications can be made without departing from the concept of the present disclosure, all of which fall within the scope of the present disclosure.

The invention claimed is:

1. A biomedical tape, comprising a dry state hydrogel carrier and a functional nanomaterial encapsulated within the dry state hydrogel carrier, wherein the dry state hydrogel carrier comprises a hyaluronic acid hydrogel thin film body and a dopamine-modified polyacrylic acid seeped into a surface of the hyaluronic acid hydrogel thin film body, the functional nanomaterial is a black phosphorus nanosheet, a hydroxyapatite nanoparticle or a gold nanoparticle.

2. The biomedical tape according to claim 1, wherein the hyaluronic acid hydrogel is a double cross-linked hyaluronic acid hydrogel obtained by physical cross-linking and photochemical cross-linking reactions with methacrylic-anhydride-modified hyaluronic acid, polyvinyl alcohol and gelatin as raw materials.

3. The biomedical tape according to claim 2, wherein in the biomedical tape, a content of the methacrylic-anhydride-modified hyaluronic acid is 12 wt % to 16 wt %, a content of the polyvinyl alcohol is 65 wt % to 70 wt %, a content of the gelatin is 5 wt % to 8 wt %, a content of the functional nanomaterial is 0.1 wt % to 0.5 wt %, and a content of the dopamine-modified polyacrylic acid is 10 wt % to 15 wt %.

4. The biomedical tape according to claim 3, wherein a number-average molecular weight of the hyaluronic acid is 50,000 to 100,000, a number-average molecular weight of the polyvinyl alcohol is 6,000 to 20,000, and a number-average molecular weight of the polyacrylic acid is 3,000 to 6,000.

5. The biomedical tape according to claim 3, wherein in terms of a total mass of the methacrylic-anhydride-modified hyaluronic acid, the methacrylic-anhydride-modified hyaluronic acid comprises 98 wt % to 99.5 wt % of hyaluronic acid and 0.5 wt % to 2 wt % of methacrylic anhydride; and in terms of a total mass of the dopamine-modified polyacrylic acid, the dopamine-modified polyacrylic acid comprises 55 wt % to 65 wt % of polyacrylic acid and 35 wt % to 45 wt % of dopamine.

6. A preparation method for a biomedical tape according to claim 1, comprising:

preparing a hyaluronic acid hydrogel with a functional nanomaterial dispersed therein;

drying and curing the hyaluronic acid hydrogel to form a film to obtain a hyaluronic acid hydrogel thin film body; and preparing a dopamine-modified polyacrylic acid solution, and making the dopamine-modified polyacrylic acid solution seep into a surface of the hyaluronic acid hydrogel thin film body by coating to obtain the biomedical tape, wherein the functional nanomaterial is a black phosphorus nanosheet, a hydroxyapatite nanoparticle or a gold nanoparticle.

7. The preparation method for the biomedical tape according to claim 6, wherein the preparing the hyaluronic acid hydrogel with the functional nanomaterial dispersed therein comprises:

preparing a methacrylic-anhydride-modified hyaluronic acid solution, a polyvinyl alcohol solution, a functional nanomaterial dispersion solution and a gelatin solution and mixing the solutions with each other to obtain a mixed reaction solution; and in the existence of a cross-linking agent and a photoinitiator, carrying out physical cross-linking and photochemical cross-linking reactions on the mixed reaction solution by illumination to obtain the hyaluronic acid hydrogel with the functional nanomaterial dispersed therein.

8. The preparation method for the biomedical tape according to claim 7, wherein in the biomedical tape, a content of the methacrylic-anhydride-modified hyaluronic acid is 12 wt % to 16 wt %, a content of the polyvinyl alcohol is 65 wt % to 70 wt %, a content of the gelatin is 5 wt % to 8 wt %, a content of the functional nanomaterial is 0.1 wt % to 0.5 wt %, and a content of the dopamine-modified polyacrylic acid is 10 wt % to 15 wt %.

9. The preparation method for the biomedical tape according to claim 8, wherein a number-average molecular weight of the hyaluronic acid is 50,000 to 100,000, a number-average molecular weight of the polyvinyl alcohol is 6,000 to 20,000, and a number-average molecular weight of the polyacrylic acid is 3,000 to 6,000.

10. The preparation method for the biomedical tape according to claim 8, wherein in terms of a total mass of the methacrylic-anhydride-modified hyaluronic acid, the methacrylic-anhydride-modified hyaluronic acid comprises 98 wt % to 99.5 wt % of hyaluronic acid and 0.5 wt % to 2 wt % of methacrylic anhydride; and in terms of a total mass of the dopamine-modified polyacrylic acid, the dopamine-modified polyacrylic acid comprises 55 wt % to 65 wt % of polyacrylic acid and 35 wt % to 45 wt % of dopamine.

11. The preparation method for the biomedical tape according to claim 6, wherein a mass concentration of the dopamine-modified polyacrylic acid solution is 5% to 10%.

12. A biomedical dressing comprising a biomedical tape, wherein the biomedical tape comprises a dry state hydrogel carrier and a functional nanomaterial encapsulated within the dry state hydrogel carrier, wherein the dry state hydrogel carrier comprises a hyaluronic acid hydrogel thin film body and a dopamine-modified polyacrylic acid seeped into a surface of the hyaluronic acid hydrogel thin film body, the functional nanomaterial is a black phosphorus nanosheet, a hydroxyapatite nanoparticle or a gold nanoparticle.

13. The biomedical dressing according to claim 12, wherein a hyaluronic acid hydrogel is a double cross-linked hyaluronic acid hydrogel obtained by physical cross-linking and photochemical cross-linking reactions with methacrylic-anhydride-modified hyaluronic acid, polyvinyl alcohol and gelatin as raw materials.

14. The biomedical dressing according to claim 13, wherein in the biomedical tape, a content of the methacrylic-anhydride-modified hyaluronic acid is 12 wt % to 16 wt %, a content of the polyvinyl alcohol is 65 wt % to 70 wt %, a content of the gelatin is 5 wt % to 8 wt %, a content of the functional nanomaterial is 0.1 wt % to 0.5 wt %, and a content of the dopamine-modified polyacrylic acid is 10 wt % to 15 wt %.

15. The biomedical dressing according to claim 14, wherein a number-average molecular weight of the hyaluronic acid is 50,000 to 100,000, a number-average molecular weight of the polyvinyl alcohol is 6,000 to 20,000, and a number-average molecular weight of the polyacrylic acid is 3,000 to 6,000.

16. The biomedical dressing according to claim 14, wherein in terms of a total mass of the methacrylic-anhydride-modified hyaluronic acid, the methacrylic-anhydride-modified hyaluronic acid comprises 98 wt % to 99.5 wt % of hyaluronic acid and 0.5 wt % to 2 wt % of methacrylic anhydride; and in terms of a total mass of the dopamine-modified polyacrylic acid, the dopamine-modified polyacrylic acid comprises 55 wt % to 65 wt % of polyacrylic acid and 35 wt % to 45 wt % of dopamine.

* * * * *